(12) United States Patent
Kornienko et al.

(10) Patent No.: US 8,349,864 B2
(45) Date of Patent: Jan. 8, 2013

(54) PYRANO [3,2-C] PYRIDONES AND RELATED HETEROCYCLIC COMPOUNDS AS PHARMACEUTICAL AGENTS FOR TREATING DISORDERS RESPONSIVE TO APOPTOSIS, ANTIPROLIFERATION OR VASCULAR DISRUPTION, AND THE USE THEREOF

(75) Inventors: Alexander Kornienko, Polvadera, NM (US); Igov V. Magedov, Socorro, NM (US); Snezna Rogelj, Socorro, NM (US)

(73) Assignee: New Mexico Technical Research Foundation, Socorro, NM (US)

( * ) Notice: Subject to any disclaimer, the term of this patent is extended or adjusted under 35 U.S.C. 154(b) by 456 days.

(21) Appl. No.: 12/407,358

(22) Filed: Mar. 19, 2009

(65) Prior Publication Data

US 2009/0247566 A1   Oct. 1, 2009

(51) Int. Cl.
*A61K 31/436* (2006.01)
(52) U.S. Cl. ......................................... 514/291; 514/302
(58) Field of Classification Search .................. None
See application file for complete search history.

(56) References Cited

U.S. PATENT DOCUMENTS

| | | | |
|---|---|---|---|
| 4,086,349 A | 4/1978 | Morinaka |
| 4,258,046 A | 3/1981 | Kämmerer |
| 4,298,610 A | 11/1981 | Morinaka |
| 5,070,088 A | 12/1991 | Atwal |
| 6,906,203 B1 | 6/2005 | Drewe |

OTHER PUBLICATIONS

Wu and Farrelly, Toxicology 236:1-6, 2007.*
Golub et al. Science (1999), vol. 286 521-537, p. 531.*
Lala et al. Cancer and Metastasis Reviews (1998), 17(1), 91-106, p. 91.*
Sausville et al., Cancer Res. (2006), vol. 66 (7), p. 3351-3354.*
Magedov et al., Bioorganic & Medicinal Chemistry Letters (2007), vol. 17, p. 3872-3876.*
Apoptosis, Wikipedia, 2011.*

* cited by examiner

*Primary Examiner* — Yong Chu
(74) *Attorney, Agent, or Firm* — Robert Becker; Robert Becker & Assoc.

(57) ABSTRACT

A pharmaceutical composition comprising a pharmaceutically acceptable excipient or carrier and a compound Formula I:

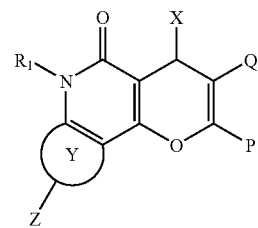

or a pharmaceutically acceptable salt or prodrug thereof.

1 Claim, 4 Drawing Sheets

PYRANO [3,2-C] PYRIDONES AND RELATED HETEROCYCLIC COMPOUNDS AS PHARMACEUTICAL AGENTS FOR TREATING DISORDERS RESPONSIVE TO APOPTOSIS, ANTIPROLIFERATION OR VASCULAR DISRUPTION, AND THE USE THEREOF

The present invention is related pharmaceutical compounds based on pyrano[3,2-c]pyridine and related fused heterocyclic scaffolds, as represented in Formula I, that are capable of treating a disorder responsive to the induction of apoptosis or antiproliferation or vascular disruption in an animal suffering from such a disorder. The present invention thus relates to the administration to an animal in need of such treatment of an effective amount of a compound of Formula I, or a pharmaceutically acceptable salt or prodrug thereof, as well as to a pharmaceutical composition comprising a pharmaceutically acceptable excipient or carrier and a compound of Formula I, or a pharmaceutically acceptable salt or prodrug thereof, as well as to a compound of Formula I, or a pharmaceutically acceptable salt or prodrug thereof.

The compounds of the present application can, for example, induce apoptosis in cancer cells without having a similar effect on non-cancerous cells. Applications for the compounds of Formula I include antiproliferation and vascular disruption agents anticancer drugs for a number of other disorders.

Due to the drug resistance of tumor cells that has developed to known anti-cancer drugs, as well as the severe side effects associated with the use of these known drugs, novel agents having an improved effectiveness and a reduced toxicity are needed. The compounds of the present application inhibit cell division by interfering with microtubule assembly to induce apoptosis (programmed cell death) in cancer cells. The compounds of the present application also interfere with microtubule assembly as vascular disrupting agents (inhibitors of growth of new blood cells). For example, necrosis can be induced in solid tumors by depriving them of oxygen and nutrients.

BRIEF DESCRIPTION OF THE DRAWINGS

To assist in explaining the present invention, the following drawings are provided, in which.

Figure 1:
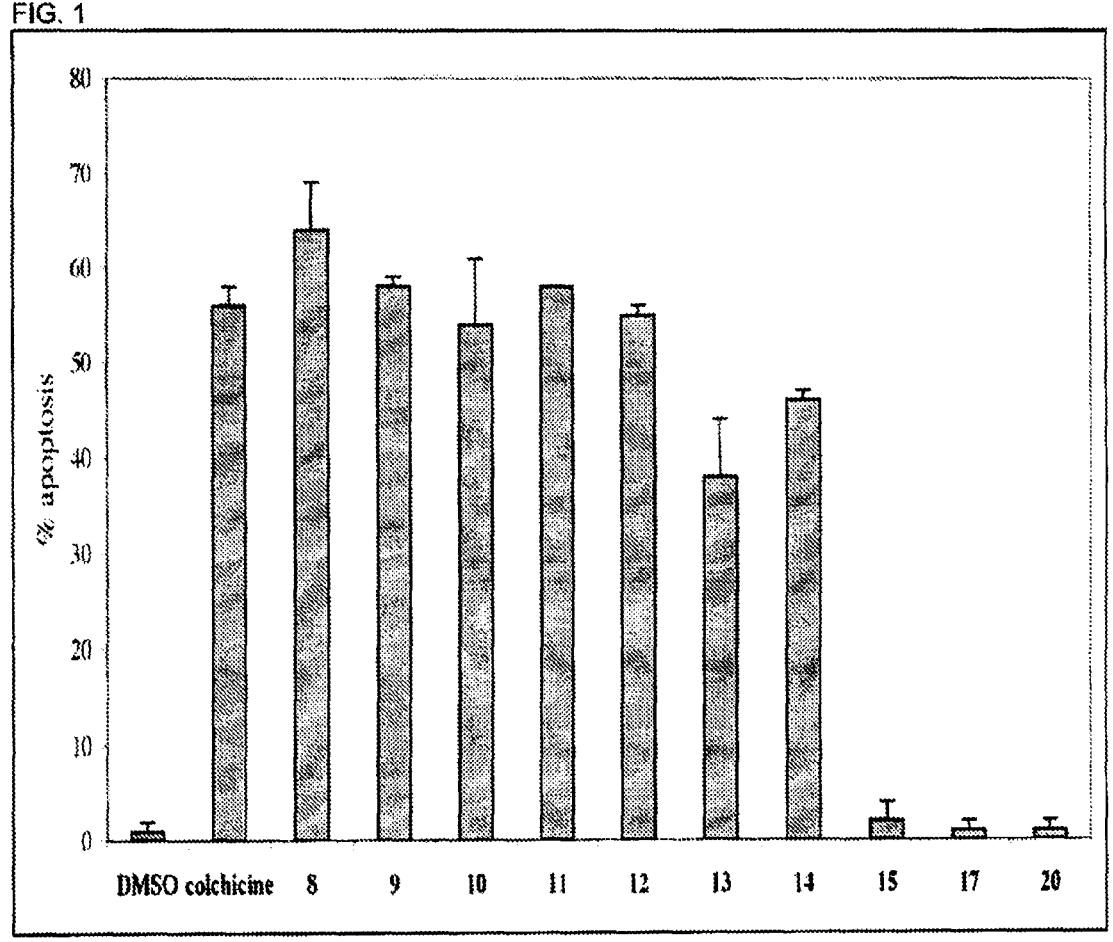
FIG. 1 shows induction of apoptosis in Jurkat cells.

General procedure for the synthesis of pyrano-[3,2-c]-pyridones and related fused heterocycles: A mixture of a required 4-hydroxypyridin-2(1H)-one (0.8 mmol), malononitrile (0.8 mmol), triethylamine (0.05 mL) and a corresponding aldehyde (0.8 mmol) in EtOH (96% aqueous solution, 3 mL) was refluxed for 50 minutes. The reaction mixture was allowed to cool to room temperature, the precipitated product was collected by filtration and washed with EtOH (5 mL). In most cases the product was >98% pure as judged by $^1$H NMR analysis. When necessary the products were recrystallized from DMF.

2-amino-5-oxo-4-(3,4,5-trimethoxyphenyl)-5,6-dihydro-4H-pyrano[3,2-c]quinoline-3-carbonitrile (1), (R═H, X═Ar, Q═CN, Y=aromatic ring, Z═H): 89%; $^1$H NMR (DMSO-d$_6$) δ 11.76 (s, 1H), 7.89 (d, J=8.0 Hz, 1H), 7.57 (m, 1H), 7.34-7.27 (m, 2H), 7.24 (s, 2H), 6.48 (s, 2H), 4.48 (s, 1H), 3.68 (s, 6H), 3.61 (s, 3H).

2-amino-4-(3-bromophenyl)-6-methyl-3-(phenylsulfonyl)-4,6-dihydro-5H-pyrano[3,2-c]quinolin-5-one (2), (R═Alk, X═Ar, Q═PhSO$_2$, Y=aromatic ring, Z═H): 92%; 8.10 (d, J=8.0 Hz, 1H), 7.67-7.14 (m, 14H), 4.76 (s, 1H), 3.50 (s, 3H).

2-Amino-4-(5-bromo-3-pyridinyl)-6-methyl-5-oxo-5,6-dihydro-4H-pyrano[3,2-c]quinoline-3-carbonitrile (3), (R═Alk, X═HetAr, Q═CN, Y=aromatic ring, Z═H): 85%; $^1$H NMR (DMSO-d$_6$) δ 8.53 (d, J=2.2 Hz, 1H), 8.50 (d, J=1.6 Hz, 1H), 8.07 (d, J=8.0 Hz, 1H), 7.84 (m, 1H), 7.74-7.69 (m, 1H), 7.56 (d, J=7.6 Hz, 1H), 7.41-7.36 (m, 1H), 7.05 (s, 2H), 4.68 (s, 1H), 3.57 (s, 3H); $^{13}$C NMR (DMSO-d$_6$) δ 160.7, 159.8, 151.3, 149.2, 145.8, 142.4, 139.7, 132.4, 122.8, 115.5, 108.0, 58.2, 36.0, 29.8; HRMS m/z (ESI) calcd for C$_{19}$H$_{13}$BrN$_4$O$_2$ (M+Na$^+$) 431.0120, found 431.0139.

4-(2-Amino-3-cyano-6-methyl-5-oxo-5,6-dihydro-4H-pyrano[3,2-c]quinolin-4-yl)-2-bromo-6-methoxyphenyl acetate (4), (R═Alk, X═Ar, Q═CN, Y=aromatic ring, Z═H): 84%; $^1$H NMR (DMSO-d$_6$) δ8.04 (d, J=8.0 Hz, 1H), 7.74-7.69 (m, 1H), 7.57 (d, J=7.6 Hz, 1H), 7.42-7.37 (m, 1H), 7.25 (s, 2H), 7.03 (s, 1H), 7.00 (s, 1H), 4.61 (s, 1H), 3.76 (s, 3H), 3.57 (s, 3H), 2.29 (s, 3H); $^{13}$C NMR (DMSO-d$_6$) δ 168.3, 160.5, 159.4, 153.2, 149.6, 142.3, 139.5, 132.8, 122.5, 122.0, 121.7, 120.4, 115.5, 108.1, 57.6, 36.8, 29.6, 20.4; HRMS m/z (ESI) calcd for C$_{23}$H$_{18}$BrN$_3$O$_5$ (M+Na$^+$) 518.0328, found 518.0334.

2-amino-4-(3-bromo-4,5-dimethoxyphenyl)-6-methyl-9-nitro-5-oxo-5,6-dihydro-4H-pyrano[3,2-c]quinoline-3-carbonitrile (5), (R═Alk, X═Ar, Q═CN, Y=aromatic ring, Z═NO$_2$): 87%; $^1$H NMR (DMSO-d$_6$) δ 8.89 (s, 1H), 8.50 (d, J=8.1 Hz, 1H), 7.77 (d, J=8.1 Hz, 1H), 7.39 (s, 2H), 7.06 (s, 1H), 6.67 (s, 1H), 4.95 (s, 1H), 3.75 (s, 3H), 3.61 (s, 3H), 3.58 (s, 3H).

2-amino-6-methyl-9-nitro-5-oxo-4-(3,4,5-trimethoxyphenyl)-5,6-dihydro-4H-pyrano[3,2-c]quinoline-3-carbonitrile (6), (R═Alk, X═Ar, Q═CN, Y=aromatic ring, Z═NO$_2$): 89%; $^1$H NMR (DMSO-d$_6$) δ 8.88 (s, 1H), 8.47 (d, J=8.0 Hz, 1H), 7.77 (d, J=8.0 Hz, 1H), 7.43 (s, 2H), 6.50 (s, 1H), 4.52 (s, 1H), 3.70 (s, 6H), 3.61 (s, 6H).

2-amino-9-bromo-4-(3-bromo-4,5-dimethoxyphenyl)-6-methyl-5-oxo-5,6-dihydro-4H-pyrano[3,2-c]quinoline-3-carbonitrile (7), (R═Alk, X═Ar, Q═CN, Y=aromatic ring, Z═Br): 92%, $^1$H NMR (DMSO-d$_6$) δ 8.18 (s, 1H), 7.86 (d, J=8.2 Hz, 1H), 7.53 (d, J=8.2 Hz, 1H), 7.25 (s, 2H), 7.05 (s, 1H), 6.64 (s, 1H), 4.93 (s, 1H), 3.75 (s, 3H), 3.60 (s, 3H), 3.50 (s, 3H).

2-Amino-4-[3-bromo-4-(dimethylamino)phenyl]-6,7-dimethyl-5-oxo-5,6-dihydro-4H-pyrano[3,2-c]pyridine-3-carbonitrile (8), (R═Alk, X═Ar, Q═CN, Y=no ring): 83%; $^1$H NMR (DMSO-d$_6$) δ 7.27-7.08 (m, 5H), 6.06 (s, 1H), 4.28 (s, 1H), 3.33 (s, 3H), 2.66 (s, 6H), 2.33 (s, 3H); $^{13}$C NMR (DMSO-d$_6$) δ 161.7, 159.8, 155.4, 153.7, 148.8, 145.0, 143.1, 122.9, 112.7, 105.5, 97.4, 60.5, 56.6, 39.3, 37.2, 31.2, 20.8; HRMS m/z (ESI) calcd for C$_{19}$H$_{19}$BrN$_4$O$_2$ (M+Na$^+$) 437.0589, found 437.0580.

2-Amino-4-(3-bromo-4,5-dimethoxyphenyl)-6,7-dimethyl-5-oxo-5,6-dihydro-4H-pyrano[3,2-c]pyridine-3-carbonitrile (9), (R═Alk, X═Ar, Q═CN, Y=no ring): 87%; $^1$H NMR (DMSO-d$_6$) δ6.93 (d, J=6.9 Hz, 2H), 6.87-6.85 (m, 2H), 6.03 (s, 1H), 4.37 (s, 1H), 3.80 (s, 3H), 3.73 (s, 3H), 3.35 (s, 3H), 2.35 (s, 3H); $^{13}$C NMR (DMSO-d$_6$) δ161.7, 159.8, 155.4, 153.6, 148.5, 145.2, 142.7, 123.2, 120.1, 116.8, 113.1, 105.6, 97.4, 60.6, 58.2, 56.8, 37.3, 31.2, 20.6; HRMS m/z (ESI) calcd for C$_{19}$H$_{18}$BrN$_3$O$_4$ (M+Na$^+$) 454.0378, found 454.0371.

2-Amino-4-(3-bromo-4-ethoxy-5-methoxyphenyl)-6,7-dimethyl-5-oxo-5,6-dihydro-4H-pyrano[3,2-c]pyridine-3- carbonitrile (10), (R=Alk, X=Ar, Q=CN, Y=no ring): 88%; $^1$H NMR (DMSO-d$_6$) δ 7.09 (s, 2H), 6.90 (s, 1H), 6.79 (s, 1H), 6.07 (d, J=2.7 Hz, 1H), 4.33 (d, J=3.0 Hz, 1H), 3.92 (q, J=3.0 Hz, 2H), 3.76 (s, 3H), 3.33 (s, 3H), 2.33 (s, 3H), 1.27 (t, J=3.0 Hz. 3H); $^{13}$C NMR (DMSO-d$_6$) δ 161.6, 159.8, 155.4, 153.8, 148.6, 144.3, 142.7, 122.9, 117.5, 112.6, 105.5, 97.42, 68.9, 57.8, 56.6, 37.1, 31.1, 20.8, 16.1; HRMS m/z (ESI) calcd for C$_{20}$H$_{20}$BrN$_3$O$_4$ (M+Na$^+$) 468.0535, found 468.0540.

2-Amino-4-(3-bromo-4-hydroxy-5-methoxyphenyl)-6,7-dimethyl-5-oxo-5,6-dihydro-4H-pyrano[3,2-c]pyridine-3-carbonitrile (11), (R=Alk, X=Ar, Q=CN, Y=no ring): 75%; $^1$H NMR (DMSO-d$_6$) δ 9.32 (s, 1H), 7.04 (s, 2H), 6.82-6.71 (m, 2H), 6.06 (s, 1H), 4.28 (s, 1H), 3.77 (s, 3H), 3.32 (s, 3H), 2.34 (s, 3H); $^{13}$C NMR (DMSO-d$_6$) δ161.6, 159.6, 155.1, 148.5, 148.4, 143.0, 137.5, 123.1, 111.5, 109.6, 105.9, 97.4, 58.0, 56.7, 37.0, 31.1, 20.8;☐ HRMS m/z (ESI) calcd for C$_{18}$H$_{16}$BrN$_3$O$_4$ (M+Na$^+$) 440.0222, found 440.0223.

4-(2-Amino-3-cyano-6,7-dimethyl-5-oxo-5,6-dihydro-4H-pyrano[3,2-c]pyridin-4-yl)-2-bromo-6-methoxyphenyl acetate (12), (R=Alk, X=Ar, Q=CN, Y=no ring): 83%; $^1$H NMR (DMSO-d$_6$) δ7.02 (s, 1H), 6.97 (s, 2H), 6.92 (s, 1H) 6.05 (s, 1H), 4.44 (s, 1H), 3.77 (s, 3H), 3.34 (s, 3H), 2.34 (s, 3H), 2.30 (s, 3H); $^{13}$C NMR (DMSO-d$_6$) δ 168.2, 161.9, 159.9, 155.6, 152.5, 148.9, 145.4, 136.5.0, 122.9, 120.2, 116.6, 112.5, 105.4, 97.4, 57.6, 56.7, 37.2, 31.1, 20.5; HRMS m/z (ESI) calcd for C$_{20}$H$_{18}$BrN$_3$O$_5$ (M+Na$^+$) 482.0328, found 482.0322.

2-Amino-4-(3-bromo-4-fluorophenyl)-6,7-dimethyl-5-oxo-5,6-dihydro-4H-pyrano[3,2-c]pyridine-3-carbonitrile (13), (R=Alk, X=Ar, Q=CN, Y=no ring): 84%; $^1$H NMR (DMSO-d$_6$) δ7.42 (m, 1H), 7.29-7.15 (m, 2H), 7.07 (s, 2H) 6.05 (s,1H), 4.37 (s,1H), 2.33 (s, 3H), 2.30 (s, 3H); $^{13}$C NMR (DMSO-d$_6$) δ161.6, 159.8, 155.35, 148.7, 143.5, 132.9, 129.3, 120.2, 117.2, 116.8, 108.1, 105.3, 97.5, 57.9, 36.8, 30.9, 20.7; HRMS m/z (ESI) calcd for C$_{17}$H$_{13}$BrFN$_3$O$_2$ (M+Na$^+$) 412.0073, found 412.0073.

2-Amino-4-(3-bromophenyl)-6,7-dimethyl-5-oxo-5,6-dihydro-4H-pyrano[3,2-c]pyridine-3-carbonitrile (14), (R=Alk, X=Ar, Q=CN, Y=no ring): 97%; $^1$H NMR (DMSO-d$_6$) δ7.39-7.11 (m, 6H), 6.07 (s, 1H), 4.35 (s, 1H), 3.30 (s, 3H), 2.34 (s, 3H); $^{13}$C NMR (DMSO-d$_6$) δ 161.5, 159.6, 155.3, 148.7, 148.1, 131.0, 130.7, 129.9, 127.2, 121.9, 120.3, 105.3, 97.4, 57.6, 37.4, 31.1, 20.5; HRMS m/z calcd for C$_{17}$H$_{14}$BrN$_3$O$_2$ (M+Na$^+$) 394.0167, found 394.0159.

2-Amino-4-(3,4-dichlorophenyl)-6,7-dimethyl-5-oxo-5,6-dihydro-4H-pyrano[3,2-c]pyridine-3-carbonitrile (15), (R=Alk, X=Ar, Q=CN, Y=no ring): 98%; $^1$H NMR (DMSO-d$_6$) δ7.54-7.49 (m, 1H), 7.38 (s, 1H), 7.18-7.16 (m, 1H), 6.83 (s, 2H), 6.03 (s, 1H), 4.43 (s, 1H) 3.35 (s, 3H), 2.35 (s, 3H); $^{13}$C NMR (DMSO-d$_6$) δ 161.6, 159.8, 155.5, 148.7, 146.4, 131.3, 130.9, 130.0, 129.8, 128.3, 119.8, 105.1, 97.3, 58.0, 36.9, 31.1, 20.4; HRMS m/z (ESI) calcd for C$_{17}$H$_{13}$Cl$_2$N$_3$O$_2$ (M+Na$^+$) 384.0283, found 384.0282.

2-Amino-6,7-dimethyl-5-oxo-4-(3,4,5-trimethoxyphenyl)-5,6-dihydro-4H-pyrano[3,2-c]pyridine-3-carbonitrile (16), (R=Alk, X=Ar, Q=CN, Y=no ring): 97%; $^1$H NMR (DMSO-d$_6$) δ 7.01 (s, 2H), 6.42 (s, 2H), 6.06 (s, 1H), 4.35 (s, 1H), 3.69 (s, 6H), 3.60 (s, 3H), 3.32 (s, 3H), 2.34 (s, 3H); $^{13}$C NMR (DMSO-d$_6$) δ 161.6, 159.8, 155.4, 153.3, 148.2, 140.9, 137.3, 120.2, 106.2, 105.6, 97.3, 60.6, 58.5, 56.4, 37.5, 31.0, 20.7; HRMS m/z (ESI) calcd for C$_{20}$H$_{21}$BrN$_3$O$_5$ (M+Na$^+$) 406.1379, found 406.1379.

2-Amino-4-(4-isopropylphenyl)-6,7-dimethyl-5-oxo-5,6-dihydro-4H-pyrano[3,2-c]pyridine-3-carbonitrile (17), (R=Alk, X=Ar, Q=CN, Y=no ring): 81%; $^1$H NMR (DMSO-d$_6$) δ7.15-7.08 (m, 4H), 6.75 (s, 2H), 6.02 (s, 1H), 4.34 (s, 1H), 3.32 (s, 3H), 2.88-2.79 (m, 1H), 2.34 (s, 3H), 1.18 (d, J=6.9 Hz, 6H); $^{13}$C NMR (DMSO-d$_6$) δ 161.7, 159.8, 155.4, 148.0, 147.0, 142.7, 127.8, 126.5, 120.2, 106.6, 97.4, 59.3, 37.2, 33.5, 31.1, 24.3, 20.6; HRMS m/z (ESI) calcd for C$_{20}$H$_{21}$N$_3$O$_2$ (M+Na$^+$) 358.1531, found 358.1519.

2-Amino-6,7-dimethyl-4-(3-nitrophenyl)-5-oxo-5,6-dihydro-4H-pyrano[3,2-c]pyridine-3-carbonitrile (18), (R=Alk, X=Ar, Q=CN, Y=no ring): 97%; $^1$H NMR (DMSO-d$_6$) δ8.04 (d, J=7.7 Hz, 1H), 7.95 (s, 1H), 7.65-7.53 (m, 2H) 6.15 (s, 2H), 6.06 (s, 1H), 4.52 (s, 1H), 3.27 (s, 3H), 2.32 (s, 3H); $^{13}$C NMR (DMSO-d$_6$) δ 161.8, 159.9, 155.6, 149.1, 148.4, 147.6, 134.9, 130.3, 122.6, 122.1, 120.1, 105.0, 97.5, 56.6, 37.4, 31.1, 20.5; HRMS m/z (ESI) calcd for C$_{17}$H$_{14}$N$_4$O$_4$ (M+Na$^+$) 361.0913, found 361.0909.

2-Amino-4-(3-bromophenyl)-7-methyl-5-oxo-4H,5H-pyrano[4,3-b]pyran-3-carbonitrile (19), (R=Alk, X=Ar, Q=CN, Y=no ring): 87%; $^1$H NMR (DMSO-d$_6$) δ7.43 (d, J=8.0 Hz, 1H), 7.38 (s, 1H), 7.32-7.27 (m, 1H), 7.21 (d, J=8.0 Hz, 1H), 7.15 (s, 2H), 6.26 (s, 1H), 4.34 (s, 1H), 2.22 (s, 3H); $^{13}$C NMR (DMSO-d$_6$) δ 163.7, 161.9, 159.1, 158.8, 146.8, 131.3, 130.8, 130.5, 127.3, 122.1, 119.5, 100.6, 98.5, 58.1, 36.6, 19.7; HRMS m/z (ESI) calcd for C$_{16}$H$_{11}$BrN$_2$O$_3$ (M+Na$^+$) 380.9845, found 380.9839.

2-Amino-6-(3,4-dimethoxyphenethyl)-7-methyl-5-oxo-4-(3,4,5-trimethoxyphenyl)-5,6-dihydro-4H-pyrano[3,2-c]pyridine-3-carbonitrile (20),

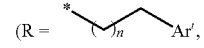

X=Ar, Q=CN, Y=no ring): 80%; $^1$H NMR (DMSO-d$_6$) δ 6.90 (s, 2H), 6.83 (d, J=8.5 Hz, 1H), 6.69-6.63 (m, 2H), 6.52 (s, 2H), 5.89 (s, 1H), 4.41 (s, 1H), 4.13-3.98 (m, 2H), 3.74 (s, 6H), 3.71 (s, 3H), 3.67 (s, 3H), 3.65 (s, 3H), 2.86-2.70 (m, 2H), 2.19 (s, 3H); $^{13}$C NMR (DMSO-d$_6$) δ 161.6, 160.0, 155.6, 153.4, 149.5, 148.4, 147.6, 141.0, 137.4, 131.4, 121.3, 120.5, 113.6, 112.9, 106.6, 105.6, 97.6, 60.5, 58.4, 56.5, 56.3, 56.1, 40.1, 37.2, 33.3, 20.0; HRMS m/z (ESI) calcd for C$_{29}$H$_{31}$N$_3$O$_7$ (M+Na$^+$) 556.2060, found 556.2057.

2-Amino-6-methyl-5-oxo-4-phenyl-5,6-dihydro-4H-pyrano[3,2-c]quinoline-3-carbonitrile (21), (R=Alk, X=Ar, Q=CN, Y=aromatic ring, Z=H): 78%; $^1$H NMR (DMSO-d$_6$) δ8.06 (d, J=7.6 Hz, 1H), 7.70-7.66 (m, 1H), 7.52 (d, J=7.6 Hz, 1H), 7.40-7.18 (m, 6H), 6.98 (s, 2H), 4.56 (s, 1H), 3.55 (s, 3H); $^{13}$C NMR (DMSO-d$_6$) δ 160.5, 159.6, 150.9, 144.9, 139.4, 132.1, 128.8, 128.0, 127.2, 122.9, 122.8, 122.6, 119.9, 115.3, 113.4, 109.8, 59.2, 37.8, 29.8; HRMS m/z (ESI) calcd for C$_{20}$H$_{15}$N$_3$O$_2$ (M+Na$^+$) 352.1062, found 352.1058.

2-Amino-6-methyl-5-oxo-4-(3,4,5-trimethoxyphenyl)-5,6-dihydro-4H-pyrano[3,2-c]quinoline-3-carbonitrile (22), (R=Alk, X=Ar, Q=CN, Y=aromatic ring, Z=H): 86%; $^1$H NMR (DMSO-d$_6$) δ8.03 (d, J=8.0 Hz, 1H), 7.72-7.66 (m, 1H), 7.55 (d, J=7.6 Hz, 1H), 7.40-7.35 (m, 1H), 7.14 (s, 2H), 6.51 (s, 2H), 4.53 (s, 1H), 3.71 (s, 6H), 3.64 (s, 3H); $^{13}$C NMR (DMSO-d$_6$) δ 160.6, 159.6, 153.4, 150.8, 140.4, 139.3, 137.5, 132.2, 122.9, 122.7, 120.1, 115.4, 113.3, 109.4, 105.9, 60.5, 58.6, 56.6, 38.2, 29.9; HRMS m/z (ESI) calcd for C$_{23}$H$_{21}$N$_3$O$_5$ (M+Na$^+$) 442.1379, found 442.1389.

2-Amino-4-(3-hydroxy-4-methoxyphenyl)-6-methyl-5-oxo-5,6-dihydro-4H-pyrano[3,2-c]quinoline-3-carbonitrile (23), (R=Alk, X=Ar, Q=CN, Y=aromatic ring, Z=H): 82%; $^1$H NMR (DMSO-d$_6$) δ8.90 (s, 1H), 8.00 (d, J=8.0 Hz, 1H), 7.72-7.67 (m, 1H), 7.55 (d, J=7.6 Hz, 1H), 7.41-7.36 (m, 1H), 7.23 (s, 2H), 6.79 (d, J=6.8 Hz, 1H), 6.61 (s, 2H), 4.37 (s, 1H), 3.71 (s, 3H), 3.55 (s, 3H); $^{13}$C NMR (DMSO-d$_6$) δ 160.3, 159.3, 150.4, 147.1, 146.8, 139.1, 137.6, 132.0, 122.8, 120.4, 118.7, 115.5, 115.1, 113.2, 112.7, 110.0, 58.8, 56.4, 37.2, 29.8; HRMS m/z (ESI) calcd for C$_{21}$H$_{17}$N$_3$O$_4$ (M+Na$^+$) 398.1117, found 398.1123.

2-Amino-4-(4-hydroxy-3-methoxyphenyl)-6-methyl-5-oxo-5,6-dihydro-4H-pyrano[3,2-c]quinoline-3-carbonitrile (24), (R=Alk, X=Ar, Q=CN, Y=aromatic ring, Z=H): 84%; $^1$H NMR (DMSO-d$_6$) δ 8.70 (s, 1H), 8.03 (d, J=7.5 Hz, 1H), 7.70-7.65 (m, 1H), 7.53 (d, J=7.6 Hz, 1H), 7.39-7.34 (m, 1H), 7.08 (s, 2H), 6.84 (s, 1H), 6.79 (d, J=8.2 Hz, 1H), 6.60-6.57 (m, 1H), 4.47 (s, 1H), 3.73 (s, 3H), 3.55 (s, 3H); $^{13}$C NMR (DMSO-d$_6$) δ 160.5, 159.5, 150.4, 147.7, 146.3, 139.3, 136.0, 132.3, 122.7, 120.4, 116.2, 115.2, 113.3, 113.1, 110.0, 59.0, 56.4, 37.1, 29.8; HRMS m/z (ESI) calcd for C$_{21}$H$_{17}$N$_3$O$_4$ (M+Na$^+$) 398.1117, found 398.1119.

2-Amino-4-(4-hydroxy-3-methoxy-5-nitrophenyl)-6-methyl-5-oxo-5,6-dihydro-4H-pyrano[3,2-c]quinoline-3-carbonitrile (25), (R=Alk, X=Ar, Q=CN, Y=aromatic ring, Z=H): 89%; $^1$H NMR (DMSO-d$_6$) δ 10.20 (s, 1H), □8.03 (d, J=8.0 Hz, 1H), 7.73-7.67 (m, 1H), 7.55 (d, J=7.6 Hz, 1H), 7.41-7.36 (m, 1H), 7.23 (s, 4H), 4.61 (s, 1H), 3.85 (s, 3H), 3.54 (s, 3H); $^{13}$C NMR (DMSO-d$_6$) δ 160.5, 159.7, 150.9, 149.9, 142.3, 139.3, 137.4, 135.8, 132.3, 122.7, 120.0, 117.2, 115.4, 114.8, 113.2, 108.7, 57.9, 57.4, 37.4, 29.9; HRMS m/z (ESI) calcd for C$_{21}$H$_{16}$N$_4$O$_6$ (M+Na$^+$) 443.0968, found 443.0966.

2-Amino-6-methyl-4-(3-nitrophenyl)-5-oxo-5,6-dihydro-4H-pyrano[3,2-c]quinoline-3-carbonitrile (26), (R=Alk, X=Ar, Q=CN, Y=aromatic ring, Z=H): 77%; $^1$H NMR (DMSO-d$_6$) δ 8.11-8.04 (m, 3H), 7.75-7.54 (m, 4H), 7.41-7.36 (m, 1H), 7.00 (s, 2H), 4.78 (s, 1H), 3.56 (s, 3H); $^{13}$C NMR (DMSO-d$_6$) δ 160.4, 160.0, 150.7, 149.9, 139.3, 134.0, 133.8, 132.4, 131.3, 128.4, 124.3, 122.9, 122.7, 119.4, 115.5, 113.1, 108.8, 56.9, 32.6, 29.8; HRMS m/z (ESI) calcd for C$_{20}$H$_{14}$N$_4$O$_4$ (M+Na$^+$) 397.0913, found 397.0917.

2-Amino-6-methyl-4-(2-nitrophenyl)-5-oxo-5,6-dihydro-4H-pyrano[3,2-c]quinoline-3-carbonitrile (27), (R=Alk, X=Ar, Q=CN, Y=aromatic ring, Z=H): 73%; $^1$H NMR (DMSO-d$_6$) δ 8.06-8.03 (m, 1H), 7.86-7.84 (m, 1H), 7.73-7.66 (m, 1H), 7.61-7.51 (m, 2H), 7.45-7.36 (m, 3H), 7.29 (s, 2H), 5.34 (s, 1H), 3.48 (s, 3H); $^{13}$C NMR (DMSO-d$_6$) δ 160.4, 160.1, 150.8, 150.0, 139.4, 134.0, 133.8, 132.4, 131.3, 128.5, 124.4, 122.8, 119.5, 115.3, 113.2, 108.8, 57.0, 32.6, 29.8; HRMS m/z (ESI) calcd for C$_{20}$H$_{14}$N$_4$O$_4$ (M+Na$^+$) 397.0913, found 397.0910.

2-Amino-6-methyl-5-oxo-4-(4-pyridinyl)-5,6-dihydro-4H-pyrano[3,2-c]quinoline-3-carbonitrile (28), (R=Alk, X=HetAr, Q=CN, Y=aromatic ring, Z=H): 79%; $^1$H NMR (DMSO-d$_6$) δ 8.45 (d, J=8.5 Hz, 2H), 8.03 (d, J=8.0 Hz, 1H), 7.73-7.67 (m, 1H), 7.54 (d, J=7.5 Hz, 1H), 7.41-7.22 (m, 5H), 4.55 (s, 1H), 3.52 (s, 3H); $^{13}$C NMR (DMSO-d$_6$) δ 160.3, 159.7, 153.1, 151.2, 150.4, 150.2, 139.3, 132.3, 123.4, 122.9, 119.8, 115.3, 113.1, 107.9, 57.0, 37.6, 29.8; HRMS m/z (ESI) calcd for C$_{19}$H$_{14}$N$_4$O$_2$ (M+Na$^+$) 353.1014, found 353.1017.

2-Amino-6-methyl-5-oxo-4-(3-pyridinyl)-5,6-dihydro-4H-pyrano[3,2-c]quinoline-3-carbonitrile (29), (R=Alk, X=HetAr, Q=CN, Y=aromatic ring, Z=H): 81%; $^1$H NMR (DMSO-d$_6$) δ 8.51 (d, J=3.6 Hz, 1H), 8.40 (m, 1H) 8.05 (m, 1H), 7.72-7.52 (m, 3H), 7.38-7.27 (m, 2H), 7.10 (s, 2H), 4.62 (s, 1H), 3.53 (s, 3H); $^{13}$C NMR (DMSO-d$_6$) δ 160.5, 159.8, 151.2, 149.8, 148.6, 140.1, 139.5, 135.5, 132.2, 124.4, 123.0, 122.6, 119.7, 115.3, 113.3, 108.7, 58.2, 35.7, 29.7; HRMS m/z (ESI) calcd for C$_{19}$H$_{14}$N$_4$O$_2$ (M+Na$^+$) 353.1014, found 453.1018.

2-Amino-4-(2-furyl)-6-methyl-5-oxo-5,6-dihydro-4H-pyrano[3,2-c]quinoline-3-carbonitrile (30), (R=Alk, X=HetAr, Q=CN, Y=aromatic ring, Z=H): 75%; $^1$H NMR (DMSO-d$_6$) δ 8.04 (d, J=8.0 Hz, 1H), 7.73-7.67 (m, 1H), 7.56 (d, J=7.6 Hz, 1H), 7.41-7.34 (m, 2H), 6.93 (s, 2H), 6.32 (s, 1H), 6.14 (d, J=6.1 Hz, 1H), 4.72 (s, 1H), 3.60 (s, 3H); $^{13}$C NMR (DMSO-d$_6$) δ 160.4, 155.9, 151.5, 142.3, 142.1, 139.4, 132.1, 122.9, 122.5, 119.5, 115.2, 113.4, 110.9, 107.2, 106.2, 56.7, 31.8, 29.9; HRMS m/z (ESI) calcd for C$_{18}$H$_{13}$N$_3$O$_3$ (M+Na$^+$) 342.0855, found 342.0851.

2-Amino-6-methyl-4-(5-methyl-2-furyl)-5-oxo-5,6-dihydro-4H-pyrano[3,2-c]quinoline-3-carbonitrile (31), (R=Alk, X=HetAr, Q=CN, Y=aromatic ring, Z=H): 78%; $^1$H NMR (DMSO-d$_6$) δ 8.03 (d, J=8.0 Hz, 1H), 7.71-7.57 (m, 2H), 7.40-7.35 (m, 1H), 7.01 (s, 2H), 5.99-5.91 (m, 2H), 4.64 (s, 1H), 3.60 (s, 3H), 2.17 (s, 3H); $^{13}$C NMR (DMSO-d$_6$) δ 160.4, 159.7, 151.5, 151.5, 145.0, 139.5, 132.5, 131.2, 129.3, 128.8, 123.1, 122.8, 119.6, 115.4, 113.1, 108.3, 56.9, 36.4, 29.9; HRMS m/z (ESI) calcd for C$_{19}$H$_{15}$N$_3$O$_3$ (M+Na$^+$) 356.1011, found 356.1022.

2-Amino-4-(2,3-dichlorophenyl)-6-methyl-5-oxo-5,6-dihydro-4H-pyrano[3,2-c]quinoline-3-carbonitrile (32), (R=Alk, X=Ar, Q=CN, Y=aromatic ring, Z=H): 95%; $^1$H NMR (DMSO-d$_6$) δ 8.05 (d, J=8.0 Hz, 1H), 7.75-7.70 (m, 1H), 7.55 (d, J=8.8 Hz, 1H), 7.48-7.38 (m, 2H), 7.27-7.14 (m, 4H), 5.15 (s, 1H), 3.52 (s, 3H); $^{13}$C NMR (DMSO-d$_6$) δ 160.4, 159.6, 151.5, 145.0, 139.5, 132.5, 131.2, 129.3, 128.8, 123.1, 122.8, 122.7, 119.6, 115.6, 115.4, 113.1, 108.3, 56.9, 36.4, 29.9; HRMS m/z (ESI) calcd for C$_{20}$H$_{13}$Cl$_2$N$_3$O$_2$ (M+Na$^+$) 420.0283, found 420.0284.

2-Amino-4-(2,6-dichlorophenyl)-6-methyl-5-oxo-5,6-dihydro-4H-pyrano[3,2-c]quinoline-3-carbonitrile (33), (R=Alk, X=Ar, Q=CN, Y=aromatic ring, Z=H): 88%; $^1$H NMR (DMSO-d$_6$) δ 8.05 (d, J=8.0 Hz, 1H), 7.72-7.67 (m, 1H), 7.55-7.21 (m, 5H), 6.91 (bs, 2H), 5.62 (s, 1H), 3.52 (s, 3H); $^{13}$C NMR (DMSO-d$_6$) δ 160.1, 139.6, 137.0, 132.4, 132.2, 129.6, 129.4, 122.8, 122.6, 122.4, 119.1, 115.1, 113.1, 106.7, 55.2, 34.6, 29.5; HRMS m/z (ESI) calcd for C$_{20}$H$_{13}$Cl$_2$N$_3$O$_2$ (M+Na$^+$) 420.0283, found 420.0280.

2-Amino-4-(3,4-dichlorophenyl)-6-methyl-5-oxo-5,6-dihydro-4H-pyrano[3,2-c]quinoline-3-carbonitrile (34), (R=Alk, X=Ar, Q=CN, Y=aromatic ring, Z=H): 97%; $^1$H NMR (DMSO-d$_6$) δ 8.03 (d, J=8.0 Hz, 1H), 7.72-7.67 (m, 1H), 7.55-7.19 (m, 7H), 4.58 (s, 1H), 3.52 (s, 3H); $^{13}$C NMR (DMSO-d$_6$) δ 160.4, 159.5, 150.9, 145.9, 139.4, 132.5, 131.4, 131.1, 130.2, 129.8, 128.5, 123.0, 122.7, 119.7, 115.5, 113.2, 108.4, 57.7, 37.3, 29.8; HRMS m/z (ESI) calcd for C$_{20}$H$_{13}$Cl$_2$N$_3$O$_2$ (M+Na$^+$) 420.0283, found 420.0274.

2-Amino-4-(3-chlorophenyl)-6-methyl-5-oxo-5,6-dihydro-4H-pyrano[3,2-c]quinoline-3-carbonitrile (35), (R=Alk, X=Ar, Q=CN, Y=aromatic ring, Z=H): 91%; $^1$H NMR (DMSO-d$_6$) δ 8.02 (d, J=8.0 Hz, 1H), 7.73-7.68 (m, 1H), 7.58-7.16 (m, 8H), 4.55 (s, 1H), 3.53 (s, 3H); $^{13}$C NMR (DMSO-d$_6$) δ 160.4, 159.5, 150.8, 147.4, 139.3, 133.4, 131.0, 128.0, 126.8, 122.8, 122.6, 120.1, 113.1, 108.7, 57.8, 37.3, 29.8; HRMS m/z (ESI) calcd for $C_{20}H_{14}ClN_3O_2$ (M+Na$^+$) 386.0673, found 386.0677.

2-Amino-4-(3-fluorophenyl)-6-methyl-5-oxo-5,6-dihydro-4H-pyrano[3,2-c]quinoline-3-carbonitrile (36), (R=Alk, X=Ar, Q=CN, Y=aromatic ring, Z=H): 90%; $^1$H NMR (DMSO-d$_6$) δ8.05-8.02 (m, 1H), 7.72-7.67 (m, 1H), 7.54 (d, J=7.5 Hz, 1H), 7.40-7.00 (m, 7H), 4.58 (s, 1H), 3.54 (s, 3H); $^{13}$C NMR (DMSO-d$_6$) δ 160.4, 159.6, 150.9, 147.8, 139.4, 132.2, 130.8, 124.0, 122.7, 119.9, 115.5, 114.9, 114.6, 114.2, 113.9, 133.2, 108.9, 58.1, 37.7, 29.9; HRMS m/z (ESI) calcd for $C_{20}H_{14}FN_3O_2$ (M+Na$^+$) 307.0968, found 370.0963.

2-Amino-4-(3-bromophenyl)-6-methyl-5-oxo-5,6-dihydro-4H-pyrano[3,2-c]quinoline-3-carbonitrile (37), (R=Alk, X=Ar, Q=CN, Y=aromatic ring, Z=H): 93%; $^1$H NMR (DMSO-d$_6$) δ8.07 (d, J=8.0 Hz, 1H), 7.73-7.68 (m, 1H), 7.57-7.24 (m, 7H), 6.98 (s, 1H), 4.59 (s, 1H), 3.57 (s, 3H); $^{13}$C NMR (DMSO-d$_6$) δ 160.5, 159.0, 151.8, 147.9, 139.3, 133.8, 131.0, 128.4, 122.8, 120.0, 113.0, 108.7, 105.4, 57.87 37.5, 29.7; HRMS m/z (ESI) calcd for $C_{20}H_{14}BrN_3O_2$ (M+Na$^+$) 430.0167, found 430.0160.

2-Amino-4-(3-bromo-4-fluorophenyl)-6-methyl-5-oxo-5,6-dihydro-4H-pyrano[3,2-c]quinoline-3-carbonitrile (38), (R=Alk, X=Ar, Q=CN, Y=aromatic ring, Z=H): 95%; $^1$H NMR (DMSO-d$_6$) δ8.03 (d, J=8.0 Hz, 1H), 7.72-7.23 (m, 8H), 4.59 (s, 1H), 3.54 (s, 3H); $^{13}$C NMR (DMSO-d$_6$) δ 160.4, 159.5, 150.9, 143.0, 139.3, 133.0, 132.8, 132.3, 129.5, 123.0, 122.8, 119.9, 117.2, 115.5, 113.2, 108.6, 58.1, 36.7, 29.7; HRMS m/z (ESI) calcd for $C_{20}H_{13}BrFN_3O_2$ (M+Na$^+$) 448.0073, found 448.0056.

2-Amino-4-(3,5-dibromo-4-hydroxyphenyl)-6-methyl-5-oxo-5,6-dihydro-4H-pyrano[3,2-c]quinoline-3-carbonitrile (39), (R=Alk, X=Ar, Q=CN, Y=aromatic ring, Z=H): 92%; $^1$H NMR (DMSO-d$_6$) δ8.03 (d, J=8.0 Hz, 1H), 7.72-7.23 (m, 8H), 4.50 (s, 1H), 3.55 (s, 3H); $^{13}$C NMR (DMSO-d$_6$) δ 160.4, 159.5, 150.9, 150.2, 139.5, 139.3, 132:2, 131.8, 123.0, 122.8, 119.9, 115.6, 113.4, 112.3, 108.7, 58.0, 37.5, 29.9; HRMS m/z (ESI) calcd for $C_{20}H_{14}Br_2N_3O_3$ (M+Na$^+$) 523.9221, found 523.9210.

2-Amino-4-(3-bromo-4-hydroxy-5-methoxyphenyl)-6-methyl-5-oxo-5,6-dihydro-4H-pyrano[3,2-c]quinoline-3-carbonitrile (40), (R=Alk, X=Ar, Q=CN, Y=aromatic ring, Z=H): 94%; $^1$H NMR (DMSO-d$_6$) δ9.16 (s, 1H), 8.02 (d, J=8.0 Hz, 1H), 7.71-7.53 (m, 2H), 7.39-7.34 (m, 1H), 7.15 (s, 2H), 6.86 (s, 1H), 6.82 (s, 1H), 4.47 (s, 1H), 3.77 (s, 3H), 3.54 (s, 3H); $^{13}$C NMR (DMSO-d$_6$) δ 160.4, 159.5, 150.6, 148.8, 143.3, 139.2, 136.9, 132.2, 123.5, 123.0, 122.7, 120.1, 115.5, 113.3, 111.8, 109.8, 109.3, 58.5, 57.0, 37.2, 29.9; HRMS m/z (ESI) calcd for $C_{21}H_{16}BrN_3O_4$ (M+Na$^+$) 476.0222, found 476.0226.

2-Amino-4-(3-bromo-4,5-dimethoxyphenyl)-6-methyl-5-oxo-5,6-dihydro-4H-pyrano[3,2-c]quinoline-3-carbonitrile (41), (R=Alk, X=Ar, Q=CN, Y=aromatic ring, Z=H): 95%; $^1$H NMR (DMSO-d$_6$) δ8.03 (d, J=8.0 Hz, 1H), 7.72-7.67 (m, 1H), 7.55 (d, J=8.0 Hz, 1H), 7.40-7.35 (m, 1H), 7.21 (s, 2H), 6.98 (d, J=1.7 Hz, 1H), 6.92 (d, J=1.7 Hz, 1H) 4.56 (s, 1H), 3.79 (s, 3H), 3.71 (s, 3H), 3.56 (s, 3H); $^{13}$C NMR (DMSO-d$_6$) δ 160.4, 159.6, 153.8, 150.9, 145.3, 142.2, 139.3, 132.3, 123.3, 123.0, 122.5, 120.1, 117.0, 115.5, 113.3, 113.0, 108.9, 60.5, 58.2, 56.5, 37.4, 29.8; HRMS m/z (ESI) calcd for $C_{22}H_{18}BrN_3O_4$ (M+Na$^+$) 490.0379, found 490.0371.

2-Amino-4-(3,5-dibromophenyl)-6-methyl-5-oxo-5,6-dihydro-4H-pyrano[3,2-c]quinoline-3-carbonitrile (42), (R=Alk, X=Ar, Q=CN, Y=aromatic ring, Z=H): 82%; $^1$H NMR (DMSO-d$_6$) δ 8.05 (d, J=8.3 Hz, 1H), 7.65-7.57 (m, 2H), 7.48-7.38 (m, 4H), 7.29 (s, 2H), 4.60 (s, 1H), 3.56 (s, 3H); $^{13}$C NMR (DMSO-d$_6$) δ 160.4, 159.7, 151.2, 149.6, 132.6, 130.1, 122.8, 115.5, 113.2, 107.8, 57.5, 37.6, 29.7; HRMS m/z (ESI) calcd for $C_{20}H_{13}Br_2N_3O_2$ (M+Na$^+$) 507.9272, found 507.9257.

2-Amino-4-(3-bromo-4-methoxyphenyl)-6-methyl-5-oxo-5,6-dihydro-4H-pyrano[3,2-c]quinoline-3-carbonitrile (43), (R=Alk, X=Ar, Q=CN, Y=aromatic ring, Z=H): 64%; $^1$H NMR (DMSO-d$_6$) δ8.02 (d, J=8.0 Hz, 1H), 7.72-7.67 (m, 1H), 7.57-7.54 (d, J=7.5 Hz, 1H), 7.38 (s, 2H), 7.22 (s, 3H), 7.01 (d, J=7.0 Hz, 1H), 4.05 (s, 1H), 3.79 (s, 3H), 3.54 (s, 3H); $^{13}$C NMR (DMSO-d$_6$) δ 160.3, 159.3, 154.7, 150.5, 139.1, 138.6, 132.4, 128.7, 122.8, 122.6, 120.2, 115.6, 113.1, 110.7, 109.1, 58.1, 56.8, 37.0, 29.8; HRMS m/z (ESI) calcd for $C_{21}H_{16}BrN_3O_3$ (M+Na$^+$) 460.0273, found 460.0287.

TABLE 1

Antiproliferative activity of pyrano-[3,2-c]-pyridones and related heterocycles.

| analogue | cell viability$^a$ GI$_{50}$, μM | |
|---|---|---|
| | HeLa | MCF-7 |
| 3 | 0.013 ± 0.003 | 0.015 ± 0.008 |

TABLE 1-continued
Antiproliferative activity of pyrano-[3,2-c]-pyridones and related heterocycles.
| analogue | structure | cell viability[a] GI$_{50}$, μM | |
|---|---|---|---|
| | | HeLa | MCF-7 |
| 4 | 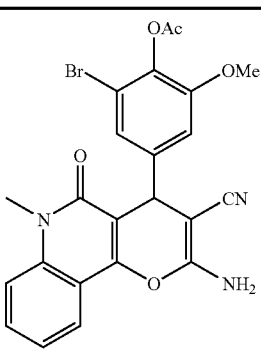 | 0.18 ± 0.02 | 0.025 ± 0.06 |
| 8 | 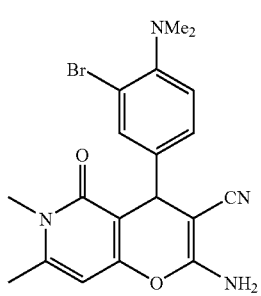 | 0.33 ± 0.06 | Not tested |
| 9 | 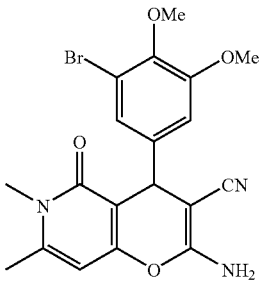 [SMILES: COc1cc(C2C(C#N)=C(N)Oc3cc(C)n(C)c(=O)c32)cc(Br)c1OC(C)=O] | 0.58 ± 0.14 | Not tested |
| 10 | 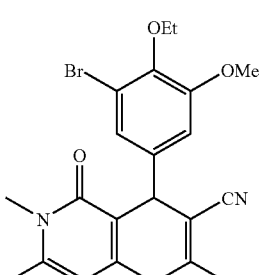 | 1.1 ± 0.8 | Not tested |
| 11 | 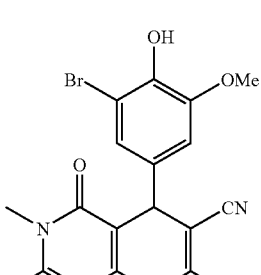 | 2.7 ± 1.1 | Not tested |

TABLE 1-continued

Antiproliferative activity of pyrano-[3,2-c]-pyridones and related heterocycles.

| analogue | structure | cell viability[a] GI$_{50}$, μM | |
|---|---|---|---|
| | | HeLa | MCF-7 |
| 12 | (3-Br, 4-OAc, 5-OMe phenyl) pyrano-pyridone | 3.5 ± 1.3 | Not tested |
| 13 | (3-Br, 4-F phenyl) pyrano-pyridone | 6.4 ± 1.1 | Not tested |
| 14 | (3-Br phenyl) pyrano-pyridone | 6.5 ± 1.3 | Not tested |
| 15 | (3,4-diCl phenyl) pyrano-pyridone | 18.3 ± 2.9 | Not tested |
| 17 | (4-isopropyl phenyl) pyrano-pyridone | >100 | Not tested |

TABLE 1-continued

Antiproliferative activity of pyrano-[3,2-c]-pyridones and related heterocycles.

| analogue | structure | cell viability[a] GI$_{50}$, μM | |
|---|---|---|---|
| | | HeLa | MCF-7 |
| 20 | | 22.7 ± 6.4 | Not tested |
| 22 | | 0.24 ± 0.02 | 1.0 ± 0.3 |
| 25 | | 0.63 ± 0.02 | 0.71 ± 0.12 |
| 37 | | 0.74 ± 0.03 | 0.003 ± 0.001 |

TABLE 1-continued
Antiproliferative activity of pyrano-[3,2-c]-pyridones and related heterocycles.
| analogue | structure | cell viability[a] GI$_{50}$, μM HeLa | MCF-7 |
|---|---|---|---|
| 38 | 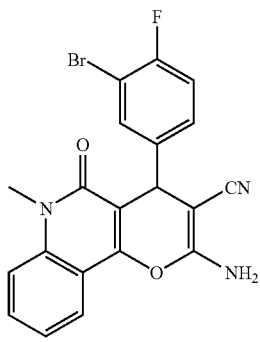 [SMILES: Cn1c(=O)c2c(c3ccccc31)OC(N)=C(C#N)C2c1ccc(F)c(Br)c1] | 0.27 ± 0.03 | 0.81 ± 0.08 |
| 39 | 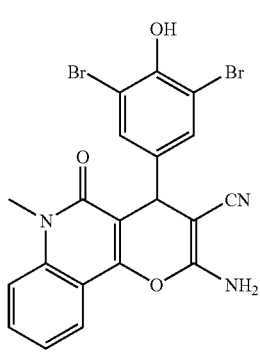 [SMILES: Cn1c(=O)c2c(c3ccccc31)OC(N)=C(C#N)C2c1cc(Br)c(O)c(Br)c1] | 0.27 ± 0.02 | 0.43 ± 0.01 |
| 40 | 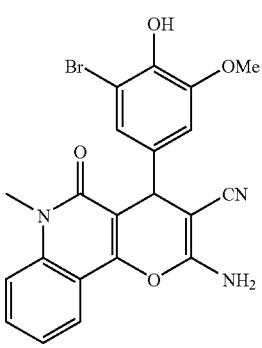 | 0.047 ± 0.010 | 0.39 ± 0.16 |
| 41 | 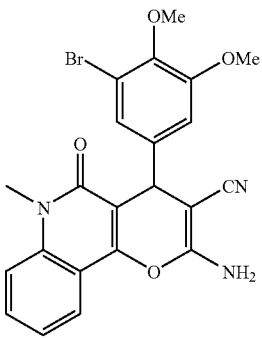 [SMILES: COc1cc(C2C(C#N)=C(N)Oc3c2c(=O)n(C)c2ccccc32)cc(Br)c1OC] | 0.014 ± 0.003 | 0.38 ± 0.03 |

TABLE 1-continued

Antiproliferative activity of pyrano-[3,2-c]-pyridones and related heterocycles.

| analogue | structure | cell viability[a] $GI_{50}$, μM | |
|---|---|---|---|
| | | HeLa | MCF-7 |
| 42 | (3,5-dibromophenyl pyranopyridone with CN, NH2) | 0.077 ± 0.006 | 0.075 ± 0.007 |
| 43 | (3-bromo-4-methoxyphenyl pyranopyridone with CN, NH2) | 0.41 ± 0.04 | 0.5 ± 0.1 |

[a] Concentration required to reduce the viability of cells by 50% after 48 h of treatment with indicated compounds relative to DMSO control ± SD from two independent experiments, each performed in 8 replicates, determined by MTT assay.

Since many clinically used anticancer agents induce apoptosis in cancer cells, we tested the pyranopyridone analogues for their ability to induce apoptosis in Jurkat (model for human T-cell leukemia) cells using the flow cytometric annexin-V/propidium iodide assay (FIG. 1). Compounds 8-14, exhibiting submicromolar or low micromolar potencies for the inhibition of proliferation of HeLa cells, were found to be strong inducers of apoptosis in Jurkat cells at 5 μM concentrations. The magnitude of apoptosis induction is comparable to the known antimitotic agent colchicine used at the same concentration. In contrast, compounds 15, 17, 20, which are much less potent or totally inactive in the HeLa MTT assay, do not induce apoptosis in Jurkat cells at this concentration.

Figure 2:
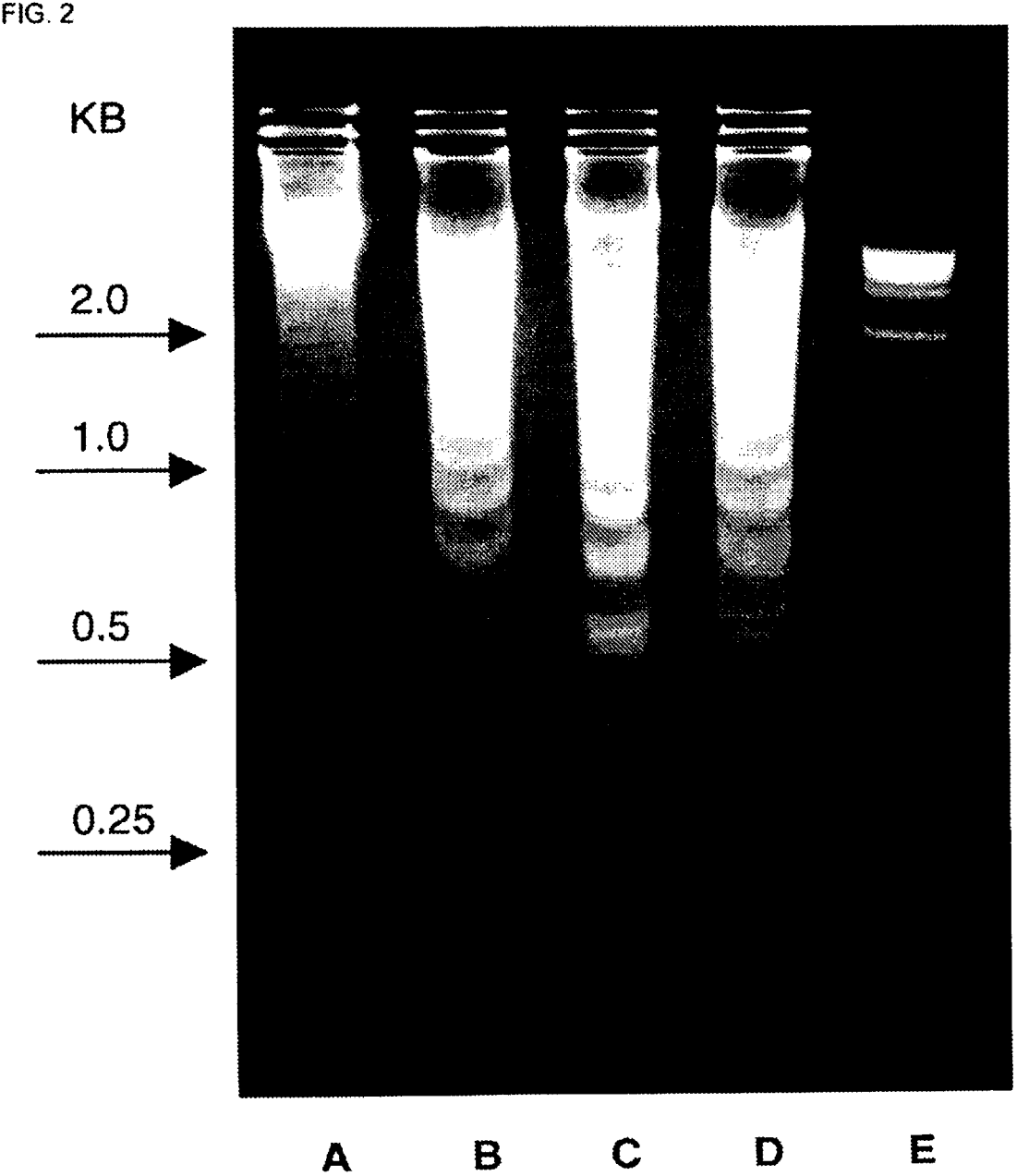
FIG. 2 shows DNA laddering in Jurkat cells.

FIG. 1 illustrates induction of apoptosis in Jurkat cells treated for 36 h with DMSO control, colchicine (5 μM) and selected pyridone library analogues (5 μM) in the flow cytometric annexin-V/propidium iodide assay. Error bars represent data Since endonuclease-mediated cleavage of nuclear DNA resulting in formation of oligonucleosomal DNA fragments (180-200 base pairs long) is a hallmark of apoptosis in many cell types, apoptosis was further investigated with the DNA laddering assay (FIG. 2). Jurkat cells were treated with DMSO (lane A), analogues 40 and 41 (lanes B and C), and paclitaxel (lane D) for 36 h. After that the cellular DNA was isolated and electrophoresed in a 1.5% agarose gel. The characteristic ladder pattern was obtained with compounds 40, 41 and paclitaxel. No laddering was observed when the cells were treated with DMSO control.

FIG. 2 illustrates DNA laddering in Jurkat cells after 36 h of treatment. (A) DMSO control, (B) 40 at 1.5 μM, (C) 41 at 1.5 μM, (D) paclitaxel at 0.4 μM, and (E) Molecular weight marker (KB).

Figure 3:
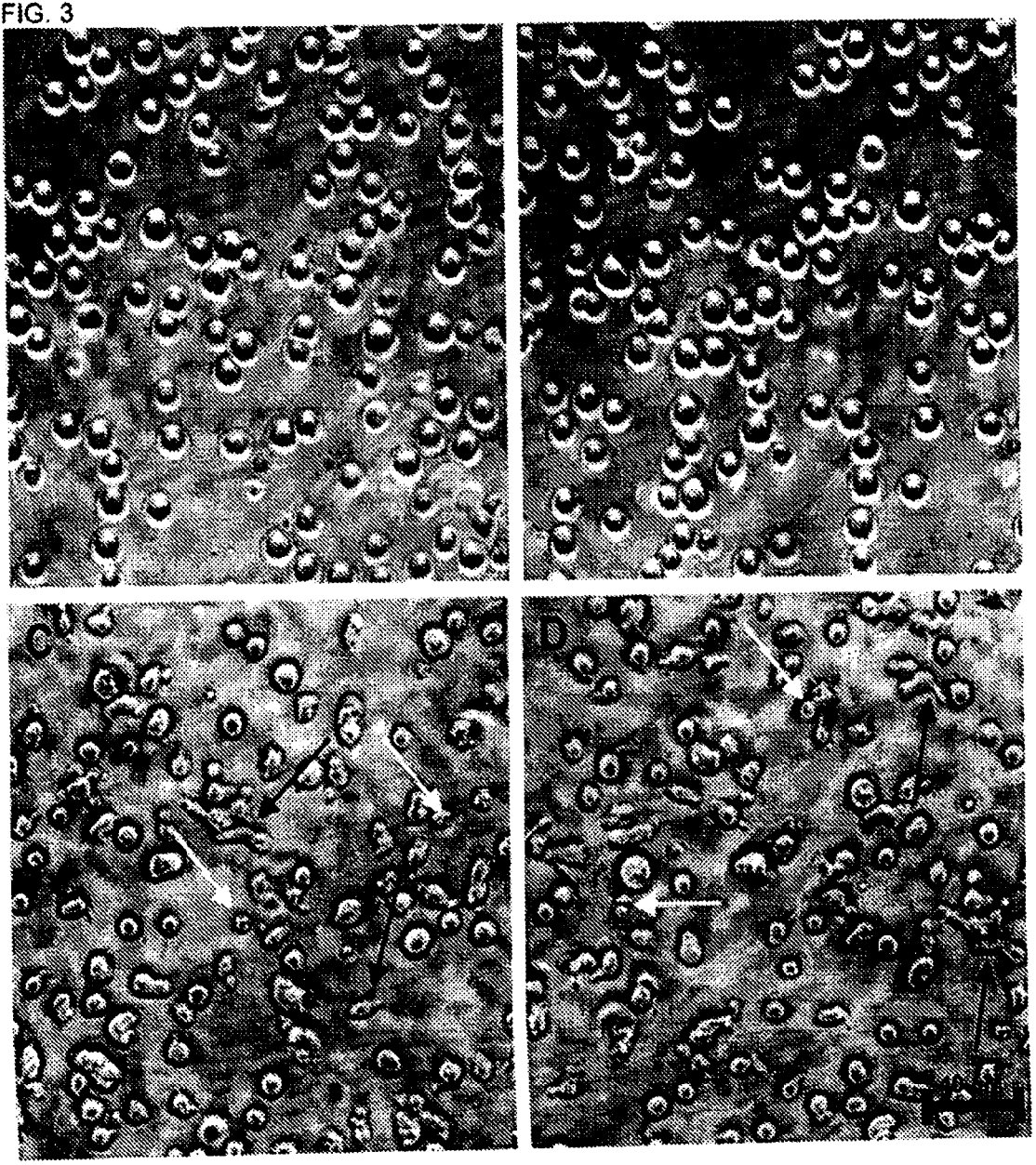
FIG. 3 shows light microscopy pictures.

Morphological changes of cells treated with potent analogues can be visually observed with light microscopy (FIG. 3). The phenotypic changes of Jurkat cells, such as formation of finger-like extensions and shriveling, become apparent as early as 2 h after their treatment with 40 (C), and 41 (D).

FIG. 3 illustrates light microscopy pictures. Treatment of Jurkat cells with 40 (C) and 41 (D) for 2 hours induces formation of finger-like extensions (black arrows) and shriveling (white arrows). 0.1% DMSO (A) and a known anticancer agent (B) were used as controls. All compounds are used at 1 μM. The scale bar indicates 40 μm.

Our libraries of compounds exert their antiproliferative properties through inhibition of tubulin dynamics, thereby inducing mitotic arrest and initiating apoptosis in cancer cells. Indeed, the flow cytometric cell cycle analysis, performed with pyranoquinolones 40 and 41 using the Jurkat cell line, shows a pronounced cell cycle arrest in the G2/M phase (Table 2). This effect is characteristic of antimitotic agents disrupting microtubule assembly.

TABLE 2

Flow cytometric cell cycle analysis of Jurkat cells.

| compound | % relative DNA content[a] | | |
|---|---|---|---|
| | G0/G1 | S | G2/M |
| DMSO | 56 ± 2 | 21 ± 3 | 20 ± 2 |
| 40 | 27 ± 3 | 22 ± 2 | 47 ± 3 |
| 41 | 20 ± 2 | 28 ± 2 | 49 ± 2 |

[a] % Relative DNA content ± SD after 24 h treatment of Jurkat cells with indicated compounds from two independent experiments each performed in triplicate. Compounds 40, 41 are used at 1 µM, obtained using the flow cytometric Vybrant Orange staining assay. The remaining % DNA content is found in sub G0/G1 region.

Figure 4:
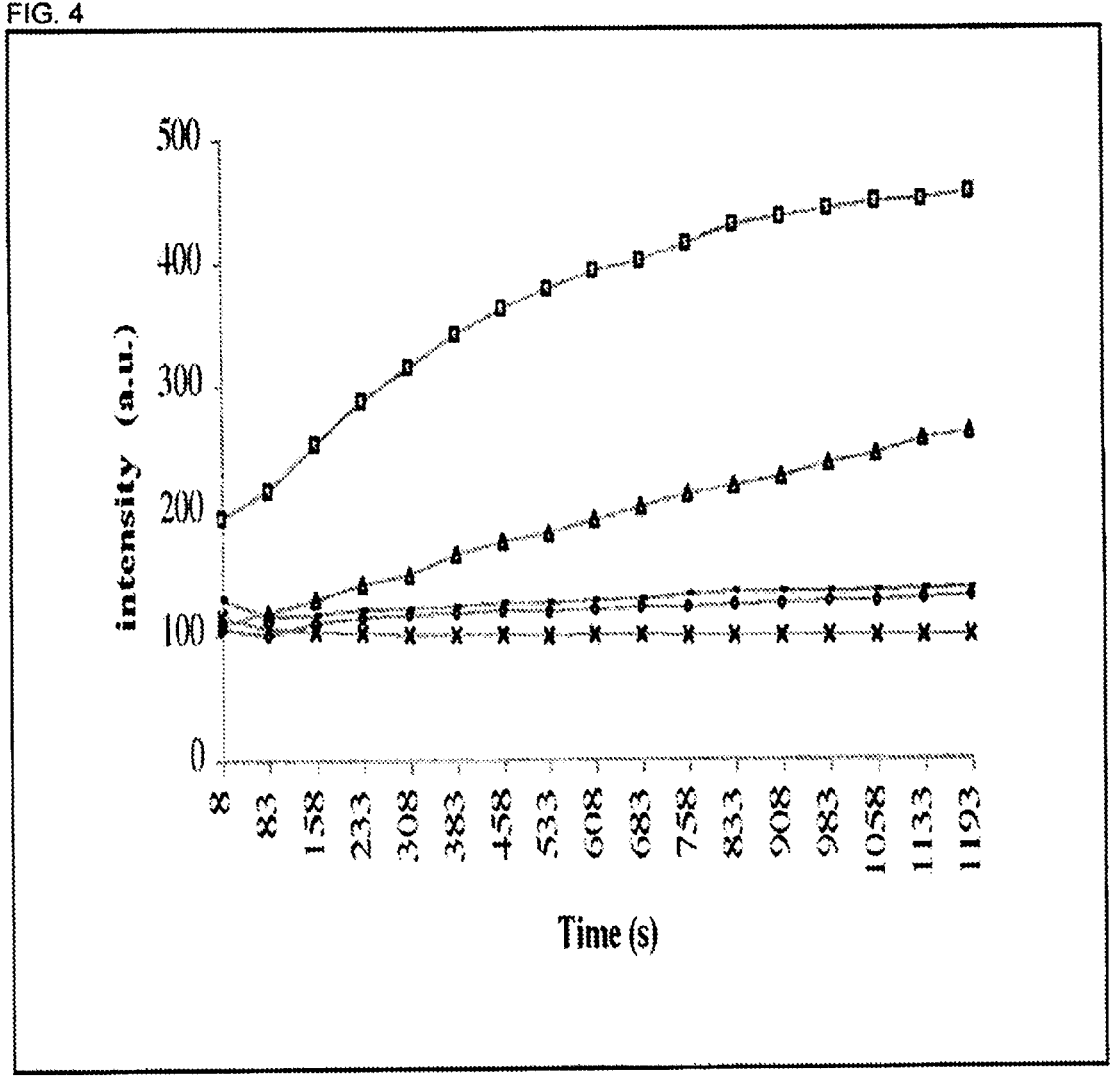
FIG. 4 shows the effect of Applicant's compounds on in vitro tubulin polymerization.

To obtain further support for the proposed antitubulin mechanism of action for our heterocycles, we assessed the effect of pyranoquinolones on in vitro tubulin polymerization. In this assay microtubule formation is monitored by the increase in fluorescence intensity of the reaction mixture. Paclitaxel exhibited potent enhancement of microtubule formation relative to the effect of DMSO control (FIG. 4). In contrast, library members 40 and 41 displayed potent microtubule destabilizing effect in a manner similar to the known tubulin polymerization inhibitor podophyllotoxin.

FIG. 4 illustrates the effect of our compounds on in vitro tubulin polymerization. Paclitaxel (3 µM, square markers) promotes microtubule formation relative to 0.05% DMSO control (triangle markers). 40 (25 µM, dash markers), 41 (25 µM, circle markers) and podophyllotoxin (25 µM, cross markers) completely suppress tubulin polymerization. Each data point is a mean of two independent experiments producing similar results.

The invention claimed is:

1. A method of treating a disorder responsive to the induction of apoptosis or antiproliferation or vascular disruption in an animal suffering therefrom, wherein the disorder is a cancer selected from the group consisting of cervical carcinoma, breast carcinoma, acute lymphatic leukemia, chronic lymphocytic leukemia, chronic granulocytic leukemia, acute granulocytic leukemia, and hairy cell leukemia, comprising administering to an animal in need of such treatment an effective amount of a compound of Formula I:

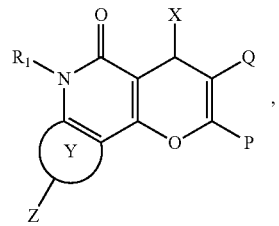

or a pharmaceutically acceptable salt thereof, wherein:
$R_1$ is hydrogen, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, carbocycloalkyl, heterocycloalkyl, hydroxyalkyl, aminoalkyl, carboxyalkyl, nitroalkyl, cyanoalkyl, acetamidoalkyl, acyloxyalkyl, hydroxyl, alkoxy, acetoxy, amino, alkylamino, acetamido;

X is optionally substituted and is aryl, heteroaryl, saturated carbocyclic, partially saturated carbocyclic, saturated heterocyclic, partially saturated heterocyclic, arylalkyl, heteroarylalkyl;

Q is CN, $COR_2$, $CO_2R_2$, $CONR_xR_y$, $CSNR_xR_y$ or $SO_2R_2$, wherein $R_2$, $R_x$ and $R_y$ are independently hydrogen, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalky, carboxyalkyl, nitroalkyl, cyanoalkyl, acetamidoalkyl, acyloxyalkyl; or $R_x$ and $R_y$ are taken together with the nitrogen to which they are attached to form a heterocycle;

P is hydrogen, halogen, $NR_3R_4$, $NHCOR_3$, $N(COR_3)_2$, $N(COR_3)(COR_4)$, $NHCONR_3R_4$, $NHCSNR_3R_4$, $N=CHOR_3$, $N=CHR_3$, wherein $R_3$ and $R_4$ are independently hydrogen, haloalkyl, $C_{1-4}$ alkyl, aryl, heteroaryl, or $R_3$ and $R_4$ are combined together with the group attached to them to form a heterocycle;

Y is no ring, aromatic ring, saturated carbocyclic ring, partially saturated carbocyclic ring, saturated heterocyclic ring, partially saturated heterocyclic ring;

Z is hydrogen, halogen, haloalkyl, $C_{1-10}$ alkyl, alkenyl, alkynyl, hydroxyalkyl, aminoalkyl, carboxyalkyl, nitroalkyl, cyanoalkyl, acetamidoalkyl, acyloxyalkyl, hydroxy, alkoxy, acetoxy, amino, alkylamino, acetamido, cyano, nitro, carobxy, thiol, azido, methylendioxy, carbonylamido, or alkysulfanyl.

* * * * *